United States Patent [19]

Cregg

[11] Patent Number: 4,837,148
[45] Date of Patent: Jun. 6, 1989

[54] AUTONOMOUS REPLICATION SEQUENCES FOR YEAST STRAINS OF THE GENUS PICHIA

[75] Inventor: James M. Cregg, San Diego, Calif.

[73] Assignee: Phillips Petroleum Company, Bartlesville, Okla.

[21] Appl. No.: 666,577

[22] Filed: Oct. 30, 1984

[51] Int. Cl.[4] .............. C12N 15/00; C12N 1/16; C12N 1/00; C07H 15/12

[52] U.S. Cl. .............. 435/172.3; 435/320; 435/91; 435/255; 435/254; 435/68; 435/938; 435/252.3; 536/27; 935/28; 935/56; 935/69; 935/29; 935/73; 935/6

[58] Field of Search .............. 536/27; 435/68, 172.3, 435/255, 317, 938, 91, 107, 254, 253, 320; 935/6, 14, 28, 37, 73, 6, 56, 69

[56] References Cited

U.S. PATENT DOCUMENTS

| | | | |
|---|---|---|---|
| 4,354,535 | 11/1982 | Pieczenik | 435/172.3 |
| 4,387,162 | 6/1983 | Angle | 435/172.3 |
| 4,617,274 | 10/1986 | Wegner | 435/255 |
| 4,628,033 | 12/1986 | DeZeeuw | 435/255 |

FOREIGN PATENT DOCUMENTS

EP-A-096910  5/1983  European Pat. Off. ......... 435/172.3

OTHER PUBLICATIONS

Russell et al., *J. Biol. Chem.*, Jan. 1983, vol. 258, pp. 143–149, "The Primary Structure of the Alcohol Dehydrogenase Gene from the Fission Yeast, *Schizosaccharomyces Pombe*".
Cryer et al, 1975, *Meth. Cell Biol*, vol. 12, pp. 39–44, Isolation of Yeast DNA.
Stinchomb et al, *Proc. Natl. Acad. Sci.*, 1980, vol. 77, pp. 6329–6333, 4559–4563, "Bukaryotic DNA Segments Capable of Autonomous Replication in Yeast".
Hinnen et al, 1978, *Proc. Natl. Acad. Sci.*, vol. 75, pp. 1929–1933, "Transformation of Yeast".
Donohue et al., *Gene*, vol. 18, pp. 47–59, "The Nucleotide Sequence of the Itisy Region of Yeast".

Primary Examiner—Robin Teskin
Attorney, Agent, or Firm—J. E. Phillips

[57] ABSTRACT

Novel autonomous replication sequences which are capable of maintaining plasmids as extrachromosomal elements in host strains of the genus Pichia are provided. In addition, novel constructs including these DNA sequences, as well as transformed organisms therewith are provided. Processes for producing the DNA sequences and constructs of the invention, as well as method for isolating such sequences from any source, are provided.

16 Claims, 8 Drawing Sheets

4,837,148

AUTONOMOUS REPLICATION SEQUENCES FOR YEAST STRAINS OF THE GENUS PICHIA

BACKGROUND

This invention relates to the field of recombinant DNA technology. In one of its aspects the invention relates to DNA fragments which are maintained as extrachromosomal elements in a host of the genus Pichia. In another aspect, the invention relates to expression vectors which incorporate the above-described DNA fragments. In yet another aspect, the invention relates to novel microorganisms transformed with the above-described expression vectors. In a further aspect, the invention relates to a process for isolating the novel DNA fragments of the invention.

The basic techniques employed in the field of recombinant DNA technology are known by those of skill in the art. The elements desirably present in order for a host mciroorganism to be useful for the practice of recombinant DNA technology include, but are not limited to:

(1) a gene encoding one or more desired polypeptide(s) and provided with adequate control sequences required for expression in the host microorganism, (2) a vector, usually a plasmid, into which the gene with control sequences can be inserted. The vector serves to guarantee transfer of the gene into the cell and maintenance of DNA sequences in the cell. Where autonomous replication sequences are included in the vector, multicopies of the vector per cell can be obtained, as well as a high level of expression of the above-mentioned gene, and (3) a suitable host mciroorganism into which the vector carrying the desired gene can be transformed, where the host microorganism also has the cellular apparatus to allow expression of the information coded for by the inserted gene.

A basic element employed in recombinant DNA technology is the plasmid, which is extrachromosomal, double-stranded DNA found in some microorganisms. Where plasmids have been found to naturally occur in microorganisms, they are often found to occur in multiple copies per cell. In addition to naturally occurring plasmids, a variety of man-made plasmids, or hybrid vectors, have been prepared. Included in the information encoded in plasmid DNA is that required to reproduce the plasmid in daughter cells, i.e., an autonomous replication sequence. One or more phenotypic selection characteristics must also be included in the information encoded in the plasmid DNA. The phenotypic selection characteristics permit clones of the host cell containing the plasmid of interest to be recognized and selected by preferential growth of the cells in selective media.

The utility of plasmids lies in the fact that they can be specifically cleaved by one or another restriction endonuclease or restriction enzyme, each of which recognizes a specific, unique site on the plasmid DNA. Thereafter, homologous genes, heterologous genes, i.e., genes derived from organisms other than the host, or gene fragments may be inserted into the plasmid by endwise joining of the cleaved plasmid and desired genetic material at the cleavage site or at reconstructed ends adjacent to the cleavage site. The resulting recombined DNA material can be referred to as a hybrid vector.

DNA recombination is performed outside the host microorganism. The resulting hybrid vector can be introduced into the host microorganism by a process known as transformation. By growing the transformed microorganism, large quantities of the hybrid vector can be obtained. When the gene is properly inserted with reference to the portions of the plasmid which govern transcription and translation of the encoded DNA message, the resulting hybrid vector can be used to direct the production of the polypeptide sequence for which the inserted gene codes. The production of polypeptide in this fashion is referred to as gene expression.

Up to now, commercial efforts employing recombinant DNA technology for producing various polypeptides have centered on *Escherichia coli* as a host organism. However, in some situations *E. coli* may prove to be unsuitable as a host. For example, *E. coli* contains a number of toxic pyrogenic factors that must be eliminated from any polypeptide useful as a pharmaceutical product. The efficiency with which this purification can be achieved will, of course, vary with the particular polypeptide. In addition, the proteolytic activities of E. coli can seriously limit yields of some useful products. These and other considerations have led to increased interest in alternative hosts, in particular, the use of eukaryotic organisms for the production of polypeptide products is appealing.

The availability of means for the production of polypeptide products in eukaryotic systems, e.g., yeast, could provide significant advantages relative to the use of prokaryotic systems such as *E. coli* for the production of polypeptides encoded by recombinant DNA. Yeast has been employed in large scale fermentations for centuries, as compared to the relatively recent advent of large scale *E. coli* fermentations. Yeast can generally be grown to higher cell densities than bacteria and are readily adaptable to continuous fermentation processing. In fact, growth of yeast such as *Pichia pastoris* to ultra-high cell densities, i.e., cell densities in excess of 100 g/L, is disclosed by Wegner in U.S. Pat. No. 4,414,329 (assigned to Phillips Petroleum Co.). Additional advantages of yeast hosts include the fact that many critical functions of the organism, e.g., oxidative phosphorylation, are located within organelles, and hence not exposed to the possible deleterious effects of the organism's production of polypeptides foreign to the wild-type host cells. As a eukaryotic organism, yeast may prove capable of glycosylating expressed polypeptide products where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA (cDNA) obtained by reverse transcription from, for example, mammalian mRNA.

The development of poorly characterized yeast species as host/vector systems is severely hampered by the lack of knowledge about transformation conditions and suitable vectors. In addition, auxotrophic mutations are often not available, precluding a direct selection for transformants by auxotrophic complementation. If recombinant DNA technology is to fully sustain its promise, new host/vector systems must be devised which facilitate the manipulation of DNA as well as optimize expression of inserted DNA sequences so that the desired polypeptide products can be prepared under controlled conditions and in high yield.

OBJECTS OF THE INVENTION

An object of the invention is therefore novel autonomous replication sequences (ARS) which maintain plasmids as extrachromosomal elements in multi-copies per cell in hosts of the genus Pichia.

Another object of the invention is novel vectors capable of maintenance as extrachromosomal elements in hosts of the genus Pichia.

Yet another object of the invention is novel yeast strains of the genus Pichia.

These and other objects of the invention will become apparent from the disclosure and claims herein provided.

STATEMENT OF THE INVENTION

In accordance with the present invention, I have discovered, isolated and characterized autonomous replication sequences which aid the maintenance of recombinant DNA material as an extrachromosomal element in multi-copy per cell in host cells of the genus Pichia. In addition, a method is provided for isolating DNA sequences having autonomous replication activity in yeast of the genus Pichia from any source of DNA.

Figure 1:
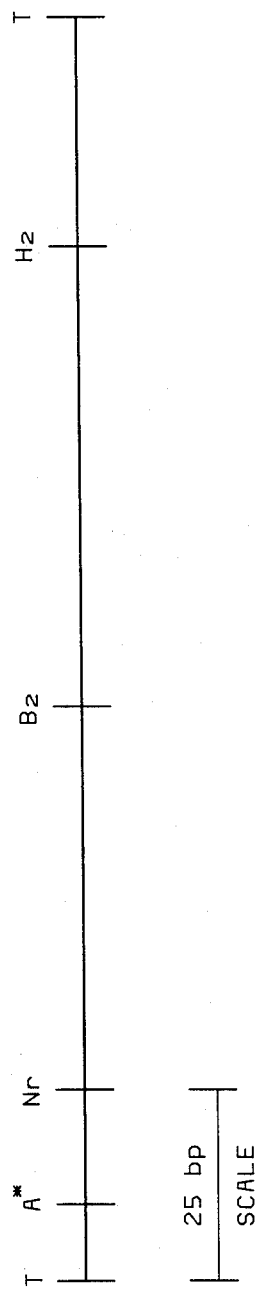
FIG. 1 is a restriction map of an autonomously replicating sequence of the invention (PARS1).

The following abbreviations are used throughout this application to represent the restriction enzymes employed:

| Abbreviation | Restriction enzyme |
|---|---|
| A | AluI |
| Ah | AhaIII |
| Av | AvaI |
| B | BamHI |
| $B_2$ | BglII |
| C | ClaI |
| $H_2$ | HindII |
| $H_3$ | HindIII |
| Mb | MboII |
| Nr | NruI |
| Ps | PstI |
| $Pv_2$ | PvuII |
| Rs | RsaI |
| $R_1$ | EcoRI |
| S | SalI |
| Sm | SmaI |
| Sp | SphI |
| $S_3$ | Sau3AI |
| T | TaqI |
| Xh | XhoI |

In the attached figures, restriction sites employed for the manipulation of DNA but which are destroyed upon ligation are indicated by enclosing the abbreviation for the destroyed site in parenthesis. Restriction sites which are predicted by nucleic acid sequence data but have not been verified by actual restriction enzyme treatment are indicated by flagging the designated restriction site with an asterisk.

DETAILED DESCRIPTION OF THE INVENTION

In accordance with the present invention, there are provided novel DNA fragments comprising autonomous replication sequences which maintain plasmids as extrachromosomal elements in hosts of the genus Pichia.

Further in accordance with the present invention, there is provided a process for isolating DNA sequences from any source which have autonomous replication properties in a host of the genus Pichia.

Host Organisms

Host organisms contemplated to be useful for the practice of the present invention include the various species of the genus Pichia. One class of useful hosts are auxotrophic mutants, i.e., mutant strains which require supplementation with one or more amino acids, vitamins or other nutrients in order to grow. Transformation of such a mutant can be readily selected by employing, as part of the recombinant DNA material used to transform the mutant host, DNA sequences which code for the production of the missing gene product.

An especially preferred host yeast strain is the mutant *Pichia pastoris* GS115, which is a mutant defective in the ability to produce histidine, and has been identified as having the mutant genotype his4. GS115 was derived by mutagenesis of *Pichia pastoris* NRRL Y-11430 and has been deposited with the Northern Regional Research Center of the United States Department of Agriculture in Peoria, Ill., in order to ensure free access of the host to the public upon issuance of this application as a patent. *Pichia pastoris* GS115 has been assigned the accession number NRRL Y-15851, as of Aug. 31, 1984. This particular host is useful because it is an auxotrophic mutant deficient in the histidine pathway. It is, of course, readily recognized by those of skill in the art that mutants in many other genes important in Pichia metabolism also exist or can be isolated. Thus, many other hosts are possible for Pichia transformation, limited only by the availability of, or ability to isolate genes which code for the production of the gene product in which the mutant host is defective.

*Pichia pastoris* NRRL Y-15851 has been identified as a mutant defective in the production of histidinol dehydrogenase. This identification was accomplished by measuring the reduction of nicotinamide adenine dinucleotide (NAD) by a protein extract from cells of NRRL Y-15851 in the presence of the histidinol dehydrogenase substrate, histidinol. By analogy to the nomenclature employed with *S. cerevisiae*, the defect in NRRL Y-15851 is referred to as a his4C mutation.

Isolation and Characterization of *Pichia pastoris* HIS4 Gene

Figure 3:
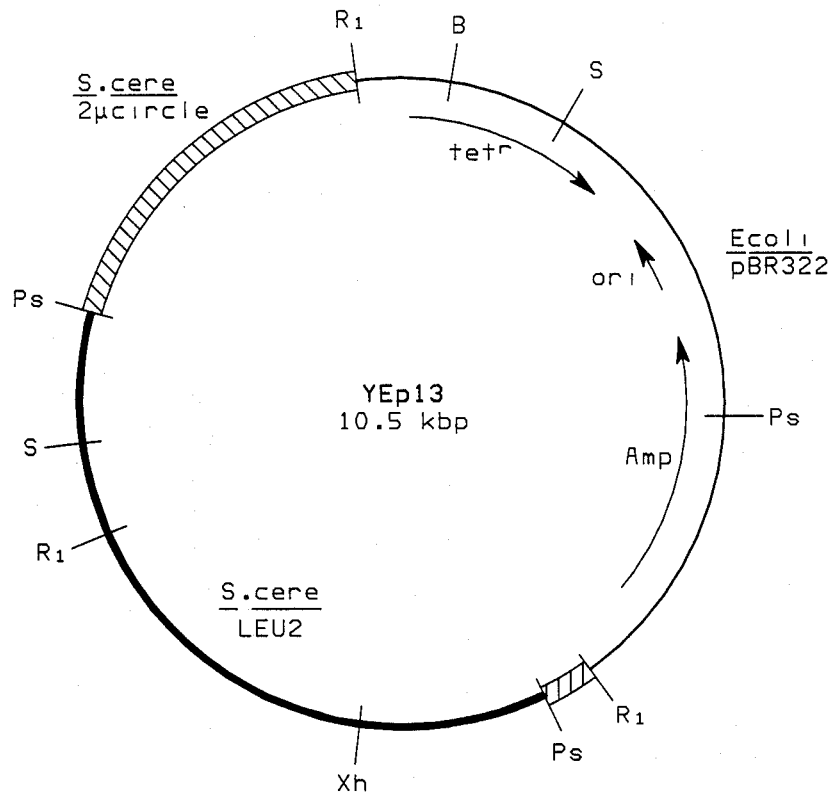
FIG. 3 is a restriction map of plasmid YEp13.
Figure 4:
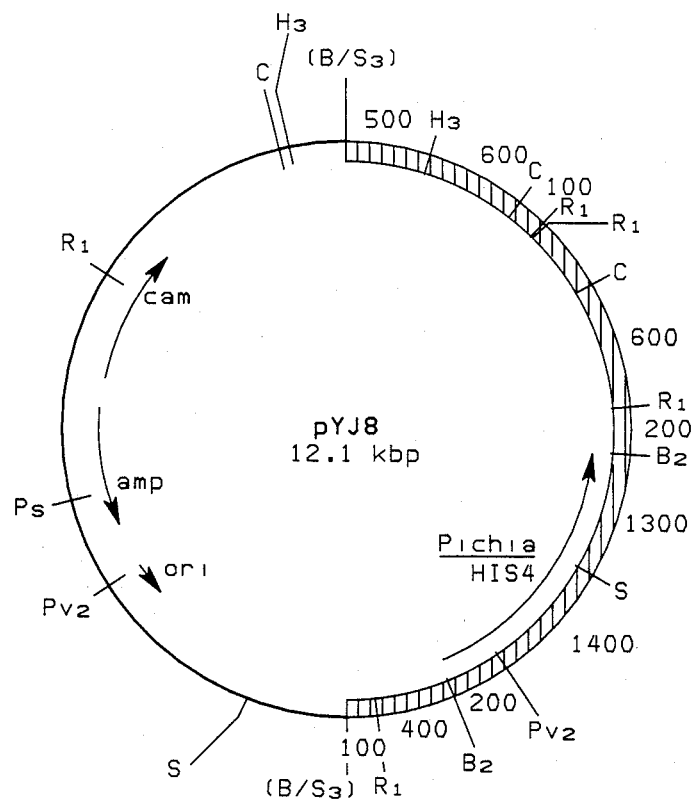
FIG. 4 is a restriction map of plasmid pYJ8.

The HIS4 gene was isolated from the strain *P. pastoris* NRRL Y-11430 by partial digestion of total chromosomal DNA with Sau3A followed by centrifugation through sucrose gradients. Fragments of 5 to 20 kbp were cloned into the BamHI cleavage site of the *S. cerevisiae-E. coli* shuttle vector YEp13 (ATCC 37115; FIG. 3) and transformed into *E. coli*. Approximately 50,000 colonies were selected and combined, then total plasmid DNA extracted. Spheroplasts of *S. cerevisiae* strain 5799–4D (NRRL Y-15859), a his4ABC mutant, were mixed with about 1 μg of the YEp13 Pichia DNA library by the procedure of Hinnen et al (1978) and allowed to regenerate in a medium deficient in histidine. The transformation resulted in about $1 \times 10^3$ protoprophic yeast colonies from a population of $5'10^7$ total regenerable spheroplasts. A parallel control sample incubated without DNA produced no colonies. Total yeast DNA was extracted from 20 of the His+ colonies and transformed back into E. coli. Seventeen of the yeast DNA preparations produced ampicillin resistant colonies. These cloned fragments were further characterized by restriction enzyme sizing and mapping as well as by their ability to cross hybridize with a labelled S. cerevisiae HIS4 fragment at low stringency (post hybridization washes in 2xSSC at 55°). The HIS4-containing fragment each contained one or more fragments which hybridized to the S. cerevisiae HIS4 gene. One such HIS4-containing plasmid was recloned to give a HIS4-containing plasmid designated pYJ8 and is shown in FIG. 4. Plasmid pYJ8 contains pBR325 sequences, including functional chloramphenicol and ampicillin resistance genes, as well as the Pichia HIS4 gene.

Figure 7:
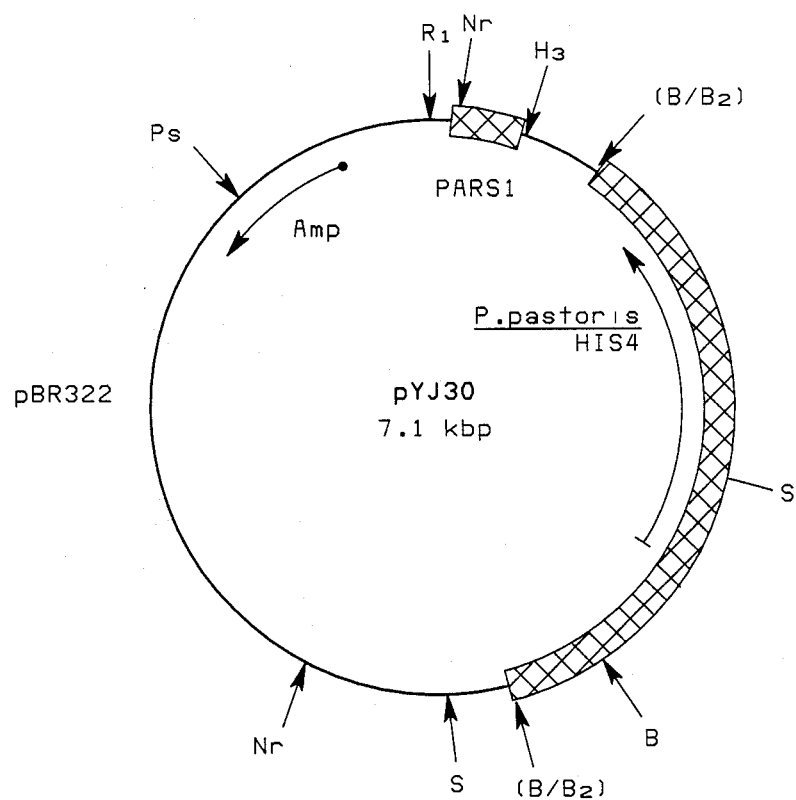
FIG. 7 is a restriction map of plasmid pYJ30.
Figure 8:
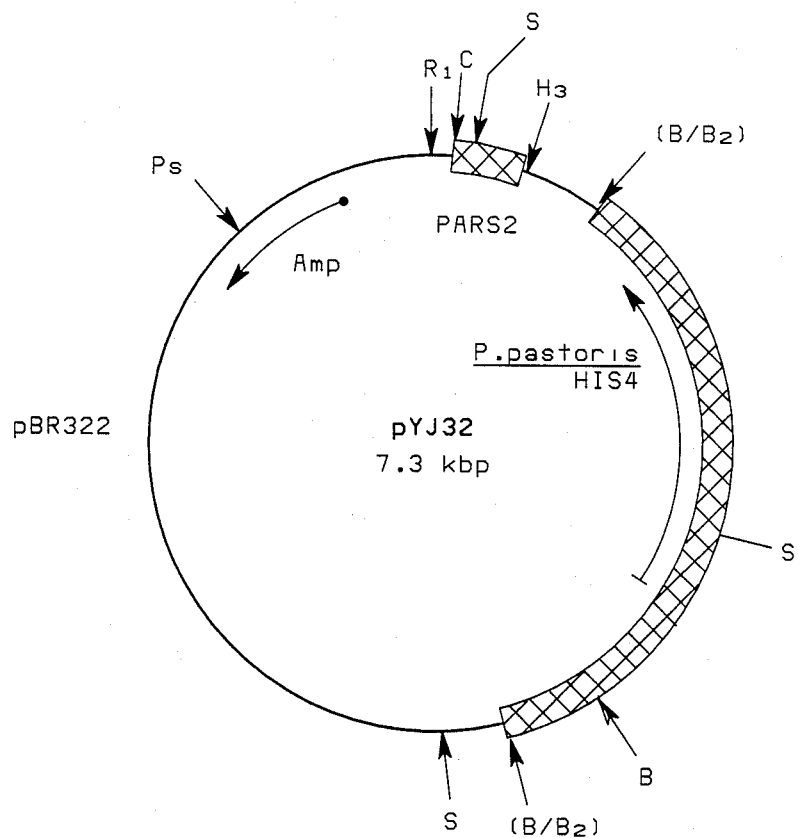
FIG. 8 is a restriction map of plasmid pYJ32.

By subcloning the 6.0 kbp Pichia DNA fragment from pYJ8, it was determined that a 2.7 kbp fragment of this DNA retained the ability to transform either Pichia or Saccharomyces strains deficient in HIS4A, HIS4B or HIS4C gene encoded activities. Thus, for example, Pichia pastoris NRRL Y-15851 (GS115), a his4 mutant, is able to grow on media without histidine supplementation when transformed with plasmids pYJ30 and pYJ32 (see FIGS. 7 and 8, respectively). These two plasmids, each of which contain the 2.7 kbp BglII fragment of Pichia chromosomal DNA, both encode the HIS4 gene function.

Pichia pastoris Transformation Procedure

The experimental procedures for transformation of Pichia pastoris are presented in greater detail below (Example I). In order to develop a transformation system for P. pastoris, the auxotrophic mutant GS115 (NRRL Y-15851) was isolated and determined to be defective in the histidine pathway in that the strain has no detectable histidinol dehydrogenase activity.

GS115 (NRRL Y-15851) can be transformed by enzymatic digestion of the cell walls to give spheroplasts; the spheroplasts are then mixed with the transforming recombinant DNA material and incubated in the presence of calcium ions and polyethylene glycol, then regenerated in selective growth medium deficient in histidine. The transforming DNA includes the HIS4 gene in which the host strain is deficient, thus only transformed cells survive on the selective growth medium employed.

Isolation of Pichia pastoris Autonomous Replication Sequences

The vectors of the present invention contain Pichia-derived autonomous replication sequences (PARSs), which enhance both the transformation frequency of GS115 (NRRL Y-15851) and the maintenance of the vectors as stable extrachromosomal elements in yeasts of the genus Pichia. These autonomous replication sequences are useful because known yeast ARS elements isolated from S. cerevisiae do not function in hosts of the genus Pichia. Thus, in order to develop Pichia as an expression system useful for the production of polypeptide products in yeast, it became necessary to isolate DNA sequences with ARS activity in Pichia.

Figure 5:
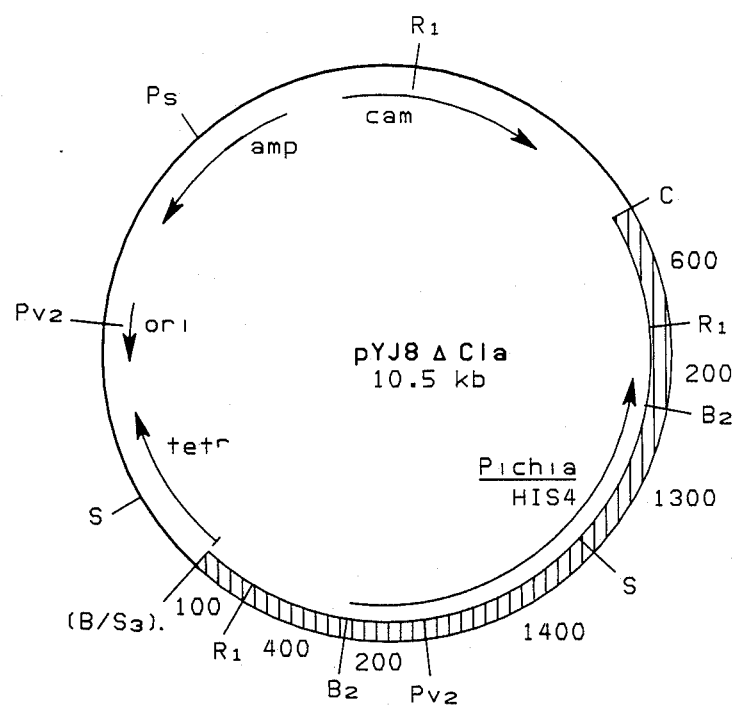
FIG. 5 is a restriction map of plasmid pYJ8ΔCla.

To search for Pichia ARSs, DNA from Pichia pastoris NRRL Y-15851 was partially digested with TaqI and 5 to 10 kbp fragments were isolated and cloned into the unique ClaI site of pYJ8ΔCla (See FIG. 5). Plasmid DNA was amplified in E. coli, recovered and used to transform Pichia pastoris NRRL Y-15851. Plasmid DNA was then recovered from about 10,000 His+-Pichia colonies and used to retransform E. coli. Plasmids from about 10,000 ampicillin resistant E. coli colonies were isolated and then transformed back into P. pastoris NRRL Y-15851 (GS115; his4). Forty of the His+ yeast colonies from this sublibrary transformation were separately streaked onto selective medium and grown independently on the selective medium. Total yeast DNA was extracted from each of these 40 cultures and transformed into E. coli. Two plasmids, pYA63, containing PARS1 and pYA90 containing PARS2 were selected for further analysis. Both of these plasmids transformed Pichia pastoris NRRL Y-15851 (GS115) at very high frequency, were maintained as autonomous elements and each contained a novel fragment of P. pastoris DNA.

Figure 6:
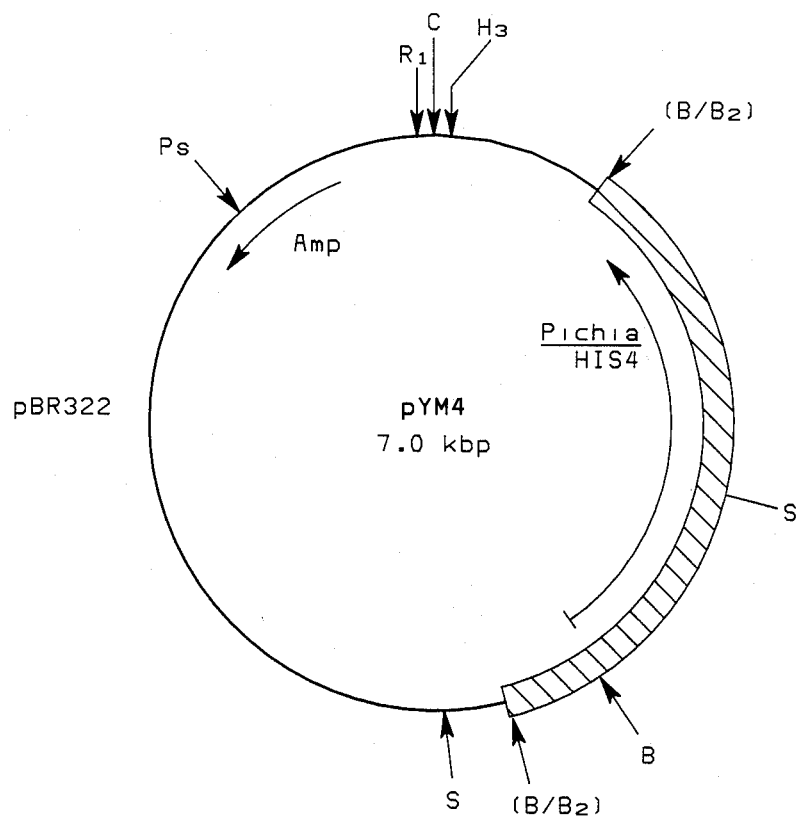
FIG. 6 is a restriction map of plasmid pYM4.

The novel autonomous replication sequences from pYA63 and pYA90 were subcloned into the unique ClaI site of plasmid pYM4 (see FIG. 6) to give plasmids pYJ30 and pYJ32, respectively. Plasmid pYJ30 is shown in detail in FIG. 7 while plasmid pYJ32 is similarly depicted in FIG. 8. The plasmids, transformed into an E. coli host, have been deposited with the Northern Regional Research Center of the U.S. Department of Agriculture, Peoria, Ill., to insure free access to the public upon issuance of this application as a patent. The deposited strains have been assigned accession numbers as follows:

| Plasmid | Host Strain | NRRL Accession No. |
|---------|-------------|--------------------|
| pYJ30   | LE392       | NRRL B-15890       |
| pYJ32   | LE392       | NRRL B-15891       |

Characterization of Pichia pastoris Autonomous Replication Sequences

Figure 2:
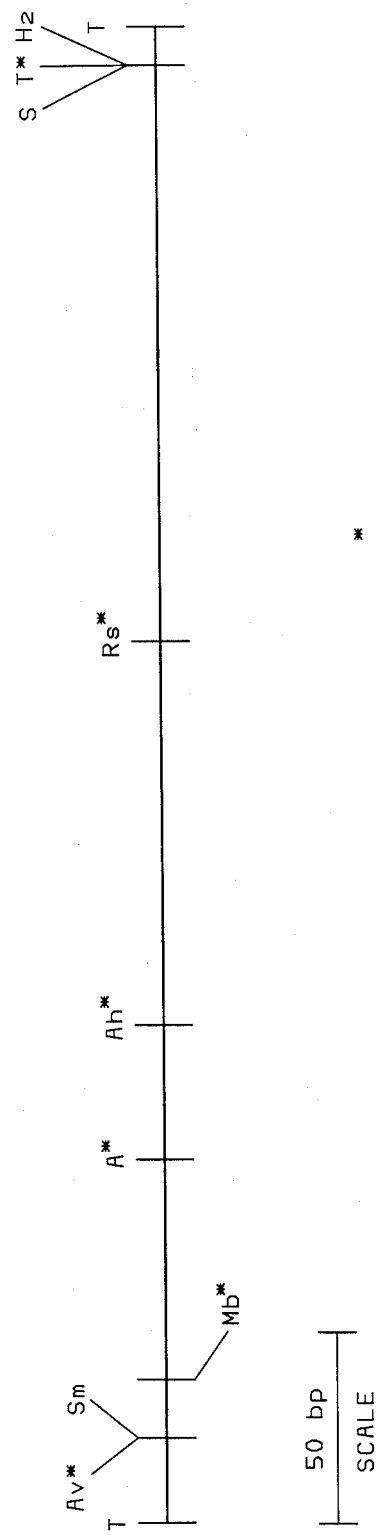
FIG. 2 is a restriction map of an autonomously replicating sequence of the invention (PARS2).

The autonomous replication sequences of the invention, PARS1 and PARS2, can conveniently be recovered from pYJ30 and pYJ32, respectively, by treating the plasmids with the restriction enzymes EcoRI and HindIII. The desired ARS element is then obtained with about 23 extra base pairs at the 5' end (adjacent to the $R_1$ site) and with about 5 extra base pairs at the 3' end (adjacent the $H_3$ site). The PARS1 and PARS2 inserts can, of course, also be recovered from pYJ30 and pYJ32 by treatment of the plasmids with a variety of other restriction enzymes, as readily recognized by those of skill in the art upon inspection of the restriction maps provided in FIGS. 7 and 8. The PARS1 and PARS2 inserts have been characterized by restriction enzyme mapping. These two DNA fragments are shown in FIGS. 1 and 2, respectively.

Due to the relatively small size of these DNA fragments, they have been completely sequenced. The nucleotide sequence for PARS1 has been determined to be:

5'-TCGAGATAAG CTGGGGGAAC ATTCGCGAAA ATGAAACAAG
   TCGGCTGTTA TAGTATATTT ATTATAATAT TGAAAGATCT
   CAAAAGACTA CTTATTTTTG AATGAACCAA GTATGAAATC
   AACCTATTTG GGGTTGACCA AAATAAGTAA ATATTAATTG
   TCGA-3'

The nucleotide sequence for PARS2 has been determined to be:

5'-TCGAACATAG TCCGTCCCCG GGGGAAGATT TATTGTCTCA
   AAAGGTCAAT TTCATATTTT ATATGCATTC AATACTTATT
   TATTATTAAT TTAGCTTGAC TACGATGCAT ATAATTTTAA
   TTTTATTTTA AATTATATAT GAGGTAAGAG TATAACTCTA
   AACCTAATAA ATATATAATT AATTATACGC AATAGTTAAA
   CCATAGATTA ATTACAACTA ATCCTTTCGT ACTAAGTTGT
   AATCCTTTAT TGACATTTCC CTAAAGCAGA TAGAAACCAT
   ACTGTCTCAC GACTATTAAA CCCAACTCAC GTAACCTTTT
   AATTGACGAA CAGTCAAACC CTTATCAGCG TGTGCTACCA
   ATAGGATAGG TTGAGTCGAC ATCGA-3'

As a measure of the ability of the PARSs to maintain plasmids as autonomous elements in Pichia, cultures of yeast cells which had been transformed with plasmids pYJ30 and pYJ32 were grown in selective medium and periodically sampled. The state of the plasmid sequences in the cells was determined by Southern hybridization of unrestricted yeast DNAs to radioactively labelled pBR322. Plasmids pYJ30 and pYJ32 were maintained as autonomous elements in Pichia for at least 50 generations in the selective medium.

An average plasmid copy number per *Pichia pastoris* cell was derived from the ratio of the amount of the genomic copy of the Pichia HIS4 gene to that of plasmid-borne HIS4 gene. For *Pichia pastoris* cells transformed with pYA63 and pYJ30 (each containing PARS1) and pYA90 and pYJ32 (each containing PARS2), the average number of copies of plasmid DNA containing the Pichia HIS4 gene relative to the number of copies of Pichia chromosomal HIS4 gene was about 10–15. It is recognized by those of skill in the art that the values for copy number derived as described herein represent minimum estimates for the number of plasmid copies per cell.

In general, DNA sequences which have autonomous replication activity in a host of the genus Pichia can be isolated by transforming the Pichia host with a library of DNA fragments constructed in a vector which contains, among other DNA sequences, a marker gene, but does not contain any DNA sequences with ARS activity in Pichia. The marker gene employed will confer a selectable phenotype upon the host yeast strain. The frequency of transformation of the host strain with the vector will be increased by one or more orders of magnitude when DNA sequences with ARS activity are present in the vector compared to the frequency of transformation with unmodified vector. Thus, selection and isolation of transformed host will provide organisms carrying plasmids with inserted DNA sequences which have ARS activity. In this fashion, DNA sequences from any source which have ARS activity in Pichia can be readily isolated.

EXAMPLES

The buffers and solutions employed in the following examples have the composition given below:

| | |
|---|---|
| 1 M Tris buffer | 121.1 g Tris base in 800 mL of H$_2$O; adjust pH to the desired value by adding concentrated (35%) aqueous HCl; allow solution to cool to room temperature before final pH adjustment; dilute to a final volume of 1L. |
| TE buffer | 1.0 mM EDTA in 0.01 M (pH 7.4) Tris buffer |
| SSC | 0.15 M NaCl<br>15 mM sodium citrate<br>adjusted to pH 7.0 with NaOH |
| Denhardts' Solution (50×) | 5 g Ficoll<br>5 g polyvinylpyrrolidone<br>5 g Bovine serum albumin (BSA; Pentax Fraction V)<br>brought to a total volume of 500 mL with water |
| LB (Luria-Bertani) Medium | 5 g Bacto-tryptone<br>5 g Bacto-yeast extract<br>2.5 g NaCl<br>in 1 L of water, adjusted to pH 7.5 with NaOH |
| YPD Medium | 1% Bacto-yeast extract<br>2% Bacto-peptone<br>2% Dextrose |
| SD Medium | 6.75 g yeast nitrogen base without amino acids (DIFCO)<br>2% Dextrose<br>in 1 L of water |
| SED | 1 M Sorbitol<br>25 mM EDTA<br>50 mM DTT |
| SCE Buffer | 9.1 g Sorbitol<br>1.47 g Sodium citrate<br>0.168 g EDTA<br>50 mL H$_2$O<br>pH to 5.8 with HCl |
| CaS | 1 M Sorbitol<br>10 mM CaCl$_2$<br>filter sterilize |
| PEG Solution | 20% polyethylene glycol-3350<br>10 mM CaCl$_2$<br>10 mM Tris-HCl (pH 7.4)<br>filter sterilize |
| SOS | 1 M Sorbitol<br>0.3 × YPD medium<br>10 mM CaCl$_2$ |

The following abbreviations are used throughout the examples with the following meaning:
EDTA: ethylenediamine tetraacetic acid
SDS: sodium dodecyl sulfate
DTT: dithiothreitol Several procedures carried out on a routine basis follow a standard protocol which will be detailed here.

Centrifugation is carried out for a period of time and at a spin rate sufficient to provide a clear supernatant. Generally, centrifugation of yeast cells is carried out at at least 1500 g for at least 5 minutes.

Nucleic acid extractions with phenol/chloroform/isoamyl alcohol involve contacting the nucleic acid containing solution with an equal volume of a 50:48:2 ratio by volume mixture of phenol, chloroform and isoamyl alcohol, respectively. Extractions with chloroform/isoamyl alcohol involve contacting the solution to be treated with an equal volume of 48:2 ratio by volume mixture of chloroform and isoamyl alcohol.

When gels, filters, etc. are described as being washed or soaked in a specified solution, the entire gel, filter, or the like was immersed in an appropriate vessel (pan, dish, vial, etc.) in order to contact the entire surface of the gel, filter, or the like with the solution of interest.

Ethanol precipitation of nucleic acids involves first adjusting the salt content of the nucleic acid-containing solution, if necessary, then contacting the solution with two volumes of cold ethanol, then collecting the precipitate by centrifugation.

EXAMPLE I

*Pichia pastoris* Transformation Procedure

A. Cell Growth

1. Inoculate a colony of *Pichia pastoris* GS115 (NRRL Y-15851) into about 10 mL of YPD medium and shake culture at 30° C. for 12-20 hrs.

2. After about 12-20 hrs., dilute cells to an $OD_{600}$ of about 0.01-0.1 and maintain cells in log growth phase in YPD medium at 30° C. for about 6-8 hrs.

3. After about 6-8 hrs, inoculate 100 mL of YPD medium with 0.5 mL of the seed culture at an $OD_{600}$ of about 0.1 (or equivalent amount). Shake at 30° C. for about 12-20 hrs.

4. Harvest culture when $OD_{600}$ is about 0.2-0.3 (after approximately 16-20 hrs) by centrifugation at 1500 g for 5 minutes.

B. Preparation of Spheroplasts

1. Wash cells once in 10 mL of sterile water. (All centrifugations for steps 1-5 are at 1500 g for 5 minutes.)

2. Wash cells once in 10 mL of freshly prepared SED.

3. Wash cells twice in 10 mL of sterile 1 M Sorbitol.

4. Resuspend cells in 10 mL SCE buffer.

5. Add 5-10 μL of 4 mg/mL Zymolyase 60,000 (Miles Laboratories). Incubate cells at 30° C. for about 30-60 minutes.

Since the preparation of spheroplasts is a critical step in the transformation procedure, one should monitor spheroplast formation as follows: add 100 μL aliquots of cells to 900 μL of 5% SDS and 900 μL of 1 M Sorbitol before or just after the addition of zymolyase and at various times during the incubation period. Stop the incubation at the point where cells lyse in SDS but not in sorbitol (usually between 30 and 60 minutes of incubation).

6. Wash spheroplasts twice in 10 mL of sterile 1 M Sorbitol by centrifugation at 1000 g for 5-10 minutes. (The time and speed for centrifugation may vary; centrifuge enough to pellet spheroplasts but not so much that they rupture from the force.)

7. Wash cells once in 10 mL of sterile CaS.

8. Resuspend cells in total of 0.6 mL of CaS.

C. Transformation

1. Add DNA samples (up to 20 μL volume) to 12×75 mm sterile polypropylene tubes. (DNA should be in water or TE buffer; for maximum transformation frequencies with small amounts of DNA, it is advisable to add about 1 μL of 5 mg/mL sonicated *E. coli* DNA to each sample.)

2. Add 100 μL of spheroplasts to each DNA sample and incubate at room temperature for about 20 minutes.

3. Add 1 mL of PEG solution to each sample and incubate at room temperature for about 15 minutes.

4. Centrifuge samples at 1000 g for 5-10 minutes and decant PEG solution.

5. Resuspend samples in 150 μL of SOS and incubate for 30 minutes at room temperature.

6. Add 850 μL of sterile 1 M Sorbitol and plate aliquots of samples as described below.

D. Regeneration of Spheroplasts

1. Recipe for Regeneration Agar Medium:

a. Agar-Sorbitol- 9 g Bacto-agar, 54.6 g Sorbitol, 240 mL $H_2O$, autoclave.

b. 10X Glucoseo- 20 g Dextrose, 100 mL $H_2O$, autoclave.

c. 10X SC- 6.75 g Yeast Nitrogen Base without amino acids, 100 mL $H_2O$, autoclave. (Add any desired amino acid or nucleic acid up to a concentration of 200 μg/mL before or after autoclaving.)

d. Add 30 mL of 10X Glucose and 30 mL of 10X SC to 300 mL of the melted Agar-Sorbitol solution. Add 0.6 mL of 0.2 mg/mL biotin and any other desired amino acid or nucleic acid to a concentration of 20 μg/mL. Hold melted Regeneration Agar at 55°-60° C.

2. Plating of Transformation Samples:

Pour bottom agar layer of 10 mL Regeneration Agar per plate at least 30 minutes before transformation samples are ready. Distribute 10 mL aliquots of Regeneration Agar to tubes in a 45°-50° C. bath during the period that transformation samples are in SOS. Add aliquots of transformation samples described above to tubes with Regeneration Agar and pour onto bottom agar layer of plates. Add a quantity of each sample to 10 mL aliquots of melted Regeneration Agar held at 45°-50° C. and pour each onto plates containing a solid 10 mL bottom agar layer of Regeneration Agar.

3. Determination of Quality of Spheroplast Preparation:

Remove 10 μL of one sample and dilute 100 times by addition to 990 μL of 1 M Sorbitol. Remove 10 μL of the 100 fold dilution and dilute an additional 100 times by addition to a second 990 μL aliquot of 1 M Sorbitol. Spread plate 100 μL of both dilutions on YPD agar medium to determine the concentration of unspheroplasted whole cells remaining in the preparation. Add 100 μL of each dilution to 10 mL of Regeneration Agar supplemented with 40 μg/mL histidine to determine total regeneratable spheroplasts. Good values for a transformation experiment are $1-3 \times 10^7$ total regeneratable spheroplasts/mL and about $1 \times 10^3$ whole cells/mL.

4. Incubate plates at 30° C. for 3-5 days.

EXAMPLE II

Isolation and Charactization of *Pichia Pastoris* Autonomous Replication Sequences A. Strains The strains employed include:

(a) *Pichia pastoris* strain NRRL Y-11430;

(b) *Pichia pastoris* NRRL Y-15851 (GS115-his4); and (c) E. coli strain 848 (F− met thi gal $T_1^R$ $\phi 80^S$ hsdR− hsdM+).

Figure 9:
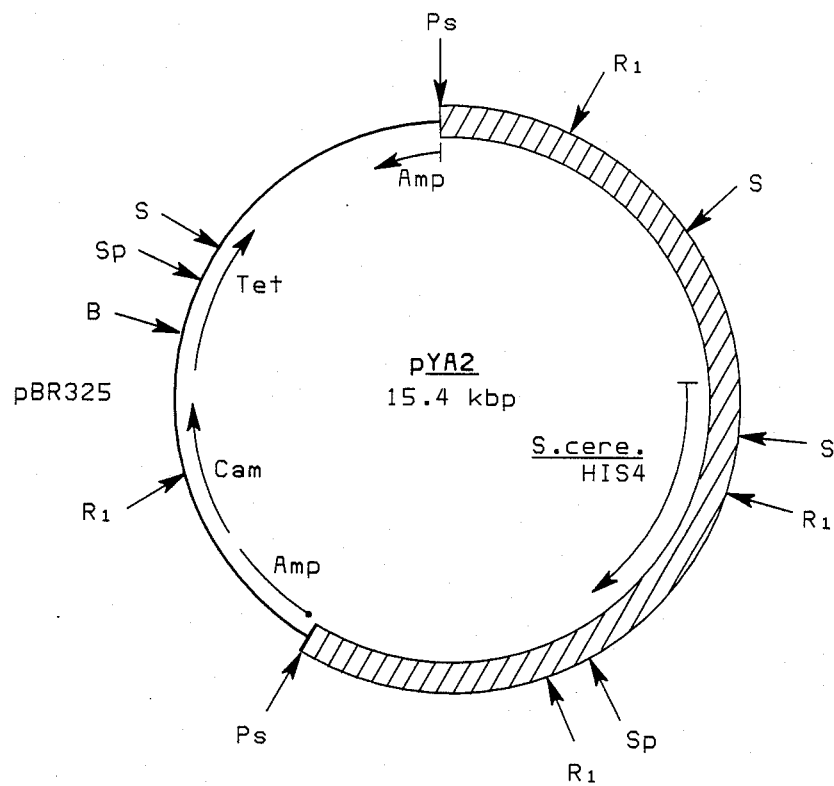
FIG. 9 is a restriction map of plasmid pYA2.

B. Plasmids pYA2 (FIG. 9) which consists of the S. cerevisiae HIS4 gene on a 9.3 kb PstI fragment inserted at the PstI site of pBR325 was the source of the S. cerevisiae HIS4 gene fragments and has been deposited in an E. coli host and is available to the public as NRRL B-15874.

pYJ8ΔCla (FIG. 5), which is a derivative of pYJ8 (FIG. 4), was created by ClaI digestion of pYJ8 and ligation.

C. Media

Pichia pastoris was grown in YPD (rich) or IMG (minimal) media. IMG, a minimal medium, consists of the following:

1. $IM_1$ Salts at a final concentration of 36.7 mM $KH_2PO_4$, 22.7 mM $(NH_4)_2SO_4$, 2.0 mM $MgSO_4\mu 7H_2O$, 6.7 mM KCl, 0.7 mM $CaCl_2.2H_2O$, prepared as a 10x stock solution and autoclaved;
2. Trace Salts at a final concentration of 0.2 μM $CuSO_4.5H_2O$, 1.25 μM KI, 4.5 μM $MnSO_4\mu H_2O$, 2.0 μM $NaMoO_4\mu 2H_2O$, 0.75 μM $H_3BO_3$, 17.5 μM $ZnSO_4.7H_2O$, 44.5 μM $FeCl_3.6H_2O$, prepared as a 400x stock solution and filter sterilized;
3. 0.4 μg/mL biotin; and
4. 2% dextrose.

E. coli was cultured in either LB medium or 2B medium (0.2% $NH_4PO_4$, 1.2% $Na_2HPO_4$, 0.013% $MgSO_4.7H_2O$, 0.074% $CaCl_2.2H_2O$, 1 μg/mL thiamine and 0.4% dextrose) supplemented with 100 μg/mL tryptophan, and 0.2% Casamino acids.

D. DNA Isolations

1. Large Scale Preparations of Yeast DNA:

Both Pichia pastoris and S. cerevisiae DNA preparations were carried out by growing yeast cells in 100 mL of minimal medium until $A_{600}$ equals 1-2 and then harvesting the cells by centrifugation at 2,000 g for 5 minutes. The cells were washed once in $H_2O$, once in SED, once in 1 M sorbitol and then suspended in 5 mL of 0.1 M Tris-HCl (pH 7.0) which is 1 M in sorbitol. The cells were mixed with 50-100 μL of a 4 mg/mL solution of Zymolase 60,000 (Miles Laboratories) and incubated at 30° C. for 1 hour to digest the cell walls. The spheroplast preparation was then centrifuged at 1000 g for 5-10 minutes and suspended in Lysis buffer (0.1% SDS, 10 mM Tris-HCl, (pH 7.4), 5 mM EDTA and 50 mM NaCl). Proteinase K (Boehringer Mannheim) and RNase A (Sigma) were each added to 100 μg/mL and the mixtures incubated at 37° C. for 30 minutes. DNA was deproteinized by gently mixing the preparation with an equal volume of chloroform containing isoamyl alcohol and the phases were separated by centrifugation at 12,0000 g for 20 minutes. The upper (aqueous) phase was drawn off into a fresh tube and extracted with an equal volume of phenol/ chloroform/isoamyl alcohol. The phases were separated as before and the top phase placed in a tube containing 2-3 volumes of cold 100% ethanol. The sample was gently mixed and DNA was collected by spooling onto a plastic rod. The DNA was immediately dissolved in 1 mL of TE buffer and dialyzed overnight at 4° C. against 100 volumes TE buffer.

2. Small Scale Yeast DNA Preparations:

Five mL of yeast cultures in minimal medium were grown until $A_{600}$ equals 1-5 and harvested by centrifugation at 2,000 g for 5 minutes. Cells were suspended in 1 mL of SED and transferred to a 1.5 mL microfuge tube, washed once in 1 M sorbitol and resuspended in 0.5 mL of 0.1 M Tris-HCl (pH 7.4) which is 1 M sorbitol. Zymolyase 60,000 (Miles Laboratories; 10 μL of a 4 mg/mL solution) was added to each sample and the cells were incubated for 30-60 minutes at 30° C. Cells were then centrifuged for 1 minute, suspended in the Lysis buffer and incubated at 65°-70° C. After 15 minutes the samples were mixed with 100 μL of 5 M potassium acetate, held in an ice bath for 15 minutes and centrifuged for 5 minutes. The supernatants were decanted into a fresh microfuge tube containing 1 mL of 100% ethanol, mixed and immediately centrifuged for 10 seconds. Finally, the DNA pellets were air dried for 10-15 minutes and dissolved in 50 μL of TE buffer.

3. Large Scale E. coli DNA Isolations:

E. coli cultures for large scale (0.5-1 L) plasmid preparations were grown at 37° C. with shaking in 2B medium supplemented as described above and with the appropriate antibiotic. For cells which contained pBR322 derived plasmids, cultures were grown to an $A_{550}$ of about 0.7 at which time sufficient chloramphenicol was added to give a concentration of 100 μg/mL and cells harvested approximately 15 hours later. Strains which contained pBR325 derived plasmids were inoculated into the supplemented 2B medium at a starting $A_{550}$ of about 0.01-0.05 and incubated with shaking at 37° C. for 20-24 hours before harvesting. Plasmids were isolated by the alkaline lysis method described by Birnboim and Doly (1979).

4. Small Scale E. coli DNA Preparations:

For small scale rapid plasmid isolations, 2 mL cultures in the supplemented 2B medium with antibiotic were grown overnight at 37° C. with shaking and harvested by centrifugation in 1.5 mL microfuge tubes. Plasmids were isolated by the alkaline lysis method described by Birnboim and Doly (1979). E. Restriction of DNA and Fragment Isolation Restriction enzymes were obtained from New England Biolabs and Bethesda Research Laboratories and digestions were performed by routine techniques. Restriction mappings were carried out by comparing parallel digestions of plasmids with and without insert DNA. Restriction fragments were purified by electroelution from agarose gels into Whatman 3 MM paper strips backed by dialysis tubing. The fragments were recovered from the paper and tubing by 3-4 washings with 0.1-0.2 mL volumes of a solution which contained 0.1 M NaCl, 50 mM Tris-HCl (pH 8.0) and 1 mM EDTA. Finally, the fragments were extracted with phenol/chloroform/isoamyl alcohol, precipitated with ethanol and redissolved in a small volume of TE buffer.

F. P. pastoris Autonomous Replication Sequence Library

Construction in E. coli.-

For the Pichia pastoris DNA-pYJ8ΔCla library construction, 50 μg of pYJ8≠Cla was digested to completion with ClaI and treated with calf intestinal alkaline phsphatase to remove the terminal 5' phosphate from the DNA. A 100 μg aliquot of DNA from Pichia pastoris NRRL Y-15851 was partially digested with 20 units of TaqI by incubation for 5 minutes at 65° C. in a total volume of 1 mL. Fragments of 5 to 10 kbp were size selected by electroelution from a 0.5% agarose gel (See Example II, Section E). One μg of the vector and 2 μg of the Pichia TaqI fragments were mixed with 20 units of T4 DNA ligase (Bethesda Research Laboratories) in a total volume of 200 μL and incubated overnight at 4° C. The ligated DNAs were transformed into E. coli by adding the entire ligation reaction mix to 2 mL of competent E. coli 848 cells and incubating for 15 minutes at 0° C. The mixture was warmed to 37° C. for 5 minutes after which time 40 mL of LB medium was added and the 37° C. incubation continued for another 1 hour. Ampicillin was then added to give a total concentration of 100 μg/mL and the incubation continued for a second hour. Finally, the cells were centrifuged for 10 minutes at 3,000 g, resuspended in 1 mL of fresh LB medium and spread in equal aliquots on 10 LB agar plates containing 100 μg/mL of ampicillin. The approximately 10,000 colonies which resulted were scraped from the plates and a portion of the cells was inoculated into 500 mL of the supplemented 2B medium at a starting $A_{550}$ of about 0.1. The culture was grown and plasmid was extracted as described above.

G. Southern Hybridizations

Hybridizations were carried out by the method described by Southern (1975). For transfer of large or supercoiled DNA molecules to nitrocellulose, DNA was first partially hydrolyzed by soaking agarose gels in 0.25 M HCl for 10 minutes prior to alkali denaturation. The hybridization of labelled fragments from the *S. cerevisiae* HIS4 gene to *Pichia pastoris* DNA was performed in the presence of 50% formamide, 6x SSC 5x Denhardt's, 0.1% SDS, 1 mM EDTA, and 100 μg/mL denatured herring sperm DNA at 42° C. Post-hybridization washes were in 2x SSC, 1 mM EDTA, 0.1% SDS and 1.0% sodium pyrophosphate at 55° C.

H. $^{32}$P-labelling

Nick translation was performed by the method described by Rigby et al (1977).

I. DNA Sequencing

DNA sequencing was by the dideoxynucleotide chain termination method of Sanger et al (1980).

J. Isolation of Pichia Autonomous Replication Sequences

The Pichia library constructed as described in Section F, above, was used to transform *Pichia pastoris* NRRL Y-15851. Plasmid DNA was amplified in *E. coli*, recovered and used to transform *Pichia pastoris* NRRL Y-15851. Plasmid DNA was then recovered from about 10,000 His+Pichia colonies and used to retransform *E. coli*. Plasmids from about 10,000 ampicillin resistant *E. coli* colonies were isolated and then transformed back into *P. pastoris* NRRL Y-15851 (GS115; his4). Forty of the His+yeast colonies from this sublibrary transformation were separately streaked onto selective medium and grown independently on the selective medium. Total yeast DNA was extracted from each of these 40 cultures and transformed into *E. coli*. Two plasmids, pYA63, containing PARS1 and pYA90 containing PARS2 were selected for further analysis. Both of these plasmids transformed *Pichia pastoris* NRRL Y-15851 (GS115) at very high frequency, were maintained as autonomous elements and each contained a novel fragment of *P. pastoris* DNA.

K. Analysis of *Pichia pastoris* Transformants for Autonomous
   Replication Sequences The ability of Pichia ARS-containing plasmids to be maintained as autonomous elements in *Pichia pastoris* cells was determined as follows: A transformant colony was picked from the regeneration agar plate and streaked onto an SD medium agar plate and inoculated into liquid IMG medium. The SD plate was incubated at 30° C. for 3 days after which time a single colony was picked from this plate, streaked onto a second SD plate and inoculated into a second flask of IMG medium. This process was repeated a third time. The 3 IMG cultures were grown at 30° C. with shaking to an $A_{600}$ of about 1-2 and then harvested by centrifugation. DNA from the yeast cultures was extracted as described above, electrophoresed at 30 Volts and 30 mAmps for 10-15 hours into 0.8% agarose gels, transferred to nitrocellulose and hybridized to $^{32}$P-labelled pBR322 or pBR325 as described above. As controls, a sample containing 10 ng of plasmid isolated from *E. coli* and a sample containing 1-2 μg of untransformed *Pichia pastoris* NRRL Y-15851 (GS115) DNA were electrophoresed in parallel with the experimental samples.

In each of the Pichia PARS-containing plasmid transformants examined, the labelled probe hybridized in a pattern identical to the plasmid DNA isolated from *E. coli*. As a control, the labelled probe was found to hybridize to high molecular weight chromosomal DNA from *Pichia pastoris* NRRL Y-15851 (GS115) when transformed with pYJ8ΔCla (an integrative transforming vector which has no ARS activity in Pichia). Probe did not hybridize to DNA from untransformed NRRL Y-15851.

As a more quantitative measure of the ability of the PARSs to maintain plasmids as autonomous elements in Pichia, cultures of yeast cells which had been transformed with plasmids pYJ30 and pYJ32 were grown in selective medium and periodically sampled. The state of the plasmid sequences in the cells was determined by Southern hybridization of unrestricted yeast DNAs to radioactively labelled pBR322. Plasmids pYJ30 and pYJ32 were maintained as autonomous elements in Pichia for at least 50 generations in the selective medium.

L. Plasmid Copy Number Determination

An average plasmid copy number per *P. pastoris* cell was derived from the ratio of the amount of the genomic copy of the *P. pastoris* HIS4 gene to that of a plasmid-borne HIS4 gene. Since the strains examined contained plasmids with the Pichia HIS4 gene, DNAs were extracted, digested with restriction endonucleases, electrophoresed into an agarose gel, transferred to a nitrocellulose filter and hybridized with a $^{32}$P-labelled 2.7 kbp BglII fragment containing the Pichia HIS4 gene. After post-hybridization washing, a series of X-ray films were exposed to the filter for specific lengths of time and scanned on a Beckman DU-8B spectrophotometer which was programmed with a Compuset Module for slab gels. Results are summarized in the Table.

TABLE

| Plasmid | Characterization of PARS-Containing *Pichia pastoris* Transformants | | | |
|---|---|---|---|---|
| | Autonomous Replication Sequence | Reference Figure | Generations as Autonomous Element | Copy Number |
| pYM4 | — | 6 | — | — |
| pYJ30 | PARS1 | 7 | 50 | 13 |
| pYJ32 | PARS2 | 8 | 50 | 13 |

Bibliography

Birnboim and Doly (1979) Nucl. Acis res. 7, 1513–1523.

Hinnen et al (1978) Proc. Nat. Acad. Sci., USA 75, 1929–1933.

Rigby et al (1977) J. Mol. Biol. 113, 237.

Southern (1975) J. Mol. Biol. 98 503–517. Sanger et al, (1980) J. mol. Biol. 143, 161–178.

I claim:

1. An isolated DNA fragment which comprises an autonomous replication sequence isolated from a strain of *Pichia pastoris;* which DNA fragment when inserted into a plasmid enables said plasmid to be maintained as an extrachromosomal element in multiple copies in a *Pichia pastoris* host, and which isolated DNA fragment when inserted into a plasmid causes increased frequency of transformation of a *Pichia pastoris* host compared to the frequency of transformation with plasmids which do not contain said isolated DNA fragment.

2. An isolated DNA fragment in accordance with claim 1 which has been isolated from *Pichia pastoris* NRRL Y-11430.

3. An isolated DNA fragment in accordance with claim 1 wherein said fragment has the nucleotide sequence:

5'-TCGAGATAAG CTGGGGGAAC ATTCGCGAAA ATGAAACAAG
TCGGCTGTTA TAGTATATTT ATTATAATAT TGAAAGATCT
CAAAAGACTA CTTATTTTTG AATGAACCAA GTATGAAATC
AACCTATTTG GGGTTGACCA AAATAAGTAA ATATTAATTG
TCGA-3'

4. An isolated DNA fragment in accordance with claim 1 wherein said fragment has the nucleotide sequence:

5'-TCGAACATAG TCCGTCCCCG GGGGAAGATT TATTGTCTCA
AAAGGTCAAT TTCATATTTT ATATGCATTC AATACTTATT
TATTATTAAT TTAGCTTGAC TACGATGCAT ATAATTTTAA
TTTTATTTTA AATTATATAT GAGGTAAGAG TATAACTCTA
AACCTAATAA ATATATAATT AATTATACGC AATAGTTAAA
CCATAGATTA ATTACAACTA ATCCTTTCGT ACTAAGTTGT
AATCCTTTAT TGACATTTCC CTAAAGCAGA TAGAAACCAT
ACTGTCTCAC GACTATTAAA CCCAACTCAC GTAACCTTTT
AATTGACGAA CAGTCAAACC CTTATCAGCG TGTGCTACCA
ATAGGATAGG TTGAGTCGAC ATCGA-3'

5. A hybrid plasmid capable of transforming a strain of *Pichia pastoris* which comprises an isolated DNA fragment in accordance with claim 1.

6. A hybrid plasmid capable of transforming a strain of *Pichia pastoris* which comprises the isolated DNA fragment of claim 3.

7. A hybrid plasmid capable of transforming a strain of *Pichia pastoris* which comprises the isolated DNA fragment of claim 4.

8. A hybrid plasmid in accordance with claim 5, which is pYJ30.

9. A hybrid plasmid in accordance with claim 5 which is pYJ32.

10. A strain of Pichia pastoris which has been transformed with the hybrid plasmid of claim 5.

11. A strain of Pichia pastoris which has been transformed with the hybrid plasmid of claim 8.

12. A strain of Pichia pastoris which has been transformed with the hybrid plasmid of claim 9.

13. *Escherichia coli* NRRL B-15890 (LE392-pYJ30).

14. *Escherichia coli* NRRL B-15891 (LE392-pYJ32).

15. A process for isolating DNA sequences from Pichia pastoris; wherein said DNA sequences have autonomous replication sequence activity in a transformable yeast host of the species Pichia pastoris; said process comprising:
(a) preparing a library of DNA fragments obtained from *Pichia pastoris* in a vector capable of transformation into a member of the species *Pichia pastoris;* wherein said vector comprises:
  (i) a marker gene; wherein said marker gene comprises a functional gene which confers a selectable phenotype upon said yeast host,
  (ii) bacterial sequences which enable transformation of bacteria with said vector, amplification of said vector in a bacterial host and selection for transformed bacterial host, but
  (iii) substantially no yeast autonomous replication sequence activity;
(b) transforming said yeast host with said library; wherein said marker gene can be selected in said yeast host;
(c) collecting transformed colonies produced in step (b) and growing them under selective conditions;
(d) extracting total DNA from the cells which survive the selective growth conditions;
(e) transforming competent *E. coli* cells with the total DNA obtained in step (d);
(f) growing the transformed *E. coli* cells obtained in step (e) under selective growth conditions, wherein said selective growth conditions comprise media plus antibiotic to which said bacterial sequences provide resistance;
(g) recovering plasmid from said transformed *E. coli* cells;
(h) transforming said yeast host with the plasmid recovered in step (g);
(i) growing up the transformed yeast host obtained in step (h) under selective growth conditions;
(j) selecting and purifying colonies which grow well under the selective growth conditions of step (i);
(k) transferring the purified colonies to liquid culture and growing under selective growth conditions
(l) extracting total DNA from the cultures grown up in liquid culture;
(m) transforming competent *E. coli* cells with the DNA isolated in step (l);
(n) selecting those colonies in step (k) which gave the high transformation frequency of *E. coli* in step (m);
(o) recovering plasmid from those colonies selected in step (n); and
(p) removing the inserted DNA fragment contained in plasmid recovered in step (o).

16. A process in accordance with claim 15 wherein said host is auxotrophic mutant *Pichia pastoris* NRRL Y-15851 (GS115).

* * * * *